United States Patent [19]

Ohyama et al.

[11] 4,255,183
[45] Mar. 10, 1981

[54] SUBSTITUTED PHENYL UREA AND HERBICIDES FOR USE IN PADDY FIELD

[75] Inventors: Hiroshi Ohyama; Sanae Takada; Yoshihisa Watanabe, all of Atsugi; Jyotaroh Tamura, Hiratsuka; Iwao Taketomi, Hatano, all of Japan

[73] Assignee: Hokko Chemical Industry Co., Ltd., Tokyo, Japan

[21] Appl. No.: 916,361

[22] Filed: Jun. 15, 1978

[30] Foreign Application Priority Data

Jun. 17, 1977 [JP] Japan ................................. 52/70990

[51] Int. Cl.³ ...................... C07C 127/19; A01N 9/20
[52] U.S. Cl. .......................................... 71/120; 564/52
[58] Field of Search ...................... 71/120; 260/553 A

[56] References Cited

U.S. PATENT DOCUMENTS

| | | | |
|---|---|---|---|
| 3,903,156 | 9/1975 | Teach | 260/553 A |
| 3,937,726 | 2/1976 | Scherer et al. | 260/553 A |
| 3,951,641 | 4/1976 | Janiak | 260/553 A X |
| 4,046,797 | 9/1977 | Cross | 260/553 A X |
| 4,046,808 | 9/1977 | Cross | 260/553 A |

FOREIGN PATENT DOCUMENTS

| | | | |
|---|---|---|---|
| 763246 | 8/1971 | Belgium | 71/120 |
| 763247 | 8/1971 | Belgium | 71/120 |
| 764863 | 9/1971 | Belgium | 71/120 |
| 1501293 | 11/1967 | France | 260/553 A |
| 2049238 | 3/1971 | France | 71/120 |
| 528861 | 11/1972 | Switzerland | 71/120 |
| 999862 | 7/1965 | United Kingdom | 260/553 A |
| 1232748 | 5/1971 | United Kingdom | 260/553 A |

OTHER PUBLICATIONS

Bertin et al., CA 72: 111120V (1970).

*Primary Examiner*—Thomas A. Waltz

[57] ABSTRACT

The invention is 3-(4-crotyloxyphenyl)-1,1-dimethyl urea herbicidal compounds.

4 Claims, No Drawings

SUBSTITUTED PHENYL UREA AND HERBICIDES FOR USE IN PADDY FIELD

This invention relates to new 3-(4-crotyloxyphenyl)-1,1-dimethyl urea (referred to hereinafter simply as "the compound of this invention)." Further, this invention relates to use of the above-named compound as a herbicide for use in paddy field. Accordingly, one object of the invention is to provide a new compound having selective herbicidal effect also on Echinochloa spp. such as *Echinochloa crus-galli var. oryzicola* at 4–5 leaves stage which have heretofore been difficult to kill in the paddy field. Another object of the present invention is to provide a new type of herbicide for use in the paddy field, characterized by containing the above compound as the effective component.

3-(4-crotyloxyphenyl)-1,1-dimethyl urea of the present invention has a substituent containing a double bond and therefore there exist isomers of trans-and cis-forms as shown by the following chemical structures:

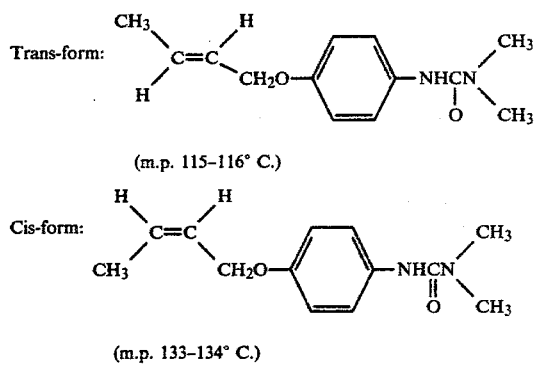

(m.p. 115–116° C.)

(m.p. 133–134° C.)

These isomers possess different physical properties. As well as the trans-form and cis-form, the present invention may include a mixture of these two forms in any proportion, and unless otherwise specifically mentioned, the expression "the compound of the invention" as used herein should be understood to include all the above compounds. *Echinochloa crus-galli var. oryzicola* to which the herbicide of the invention is primarily applied is the most typical plant of Echinochloa spp. appearing in paddy field and is a kind of barnyard grass. *Echinochloa crus-galli var. oryzicola* can grow from a shallow region to considerably deep region of submerging depth. The state of the yound plants closely resembles to that of rice but its growth is more quick than rice. When *Echinochloa crus-galli var. oryzicola* grows to adult plant, its height is greater than that of rice and so it becomes outstanding, showing its ear above rice. If *Echinochloa crus-galli var. oryzicola* grows thick, paddy rice is shaded and the amount of light received by paddy rice is limited. Thus, the function of paddy rice for photosynthesis or for nutrient absorption is lowered, resulting in inhibition of the growth of paddy rice with an adverse effect on the harvest amount. Further, in accordance with recent spread of various agricultural machines, for example, a combine, when *Echinochloa crus-galli var. oryzicola* is retained at the harvesting, seeds thereof are admixed into harvested rice, causing thereby reduction in the quality of rice. Therefore, it has been a problem of importance in the cultivation of paddy rice how to effectively kill the plants of Echinochloa spp. such as *Echinochloa crus-galli var. oryzicola*.

Heretofore, a number of new herbicides have been developed and put into practice in order to solve such problem. As examples of such herbicides, there can be included those for use in paddy field, which contain, as effective components, 2,4-dichlorophenyl-4'-nitrophenylether (NIP), 2,4,6-trichlorophenyl-4'-nitrophenylether (CNP), 2,4-dichlorophenyl-3'-methoxy-4'-nitrophenylether (Chlomethoxynil), 5-tert.butyl-3-(2,4-dichloro-5-isopropoxyphenyl)-1,3,4-oxadiazol-2-one (Oxadiazon), 2-chloro-2',6'-diethyl-N-(butoxymethyl)-acetanilide (Butachlor), 2,4-bis(ethylamino)-6-methylthio-1,3,5-triazine (Simetryne), s-ethyl hexahydro-1H-azepine-1-carbothioate (Molinate), 4-chlorobenzyl-N,N-diethylthiolcarbamate (Benthiocarb), N-(0,0-di-n-porpyldithiophosphorylacetyl)-2-methylpiperidine (Piperophos), etc.

These herbicides exhibit herbicidal effect on *Echinochloa crus-galli var. oryzicola* at the stage from pre-emergence to about two-leaf stage. The initial growth stage of *Echinochloa crus-galli var. oryzicola* is, in a transplanted paddy field, before or after the transplantation of paddy rice and, in a directly seeded paddy field, the initial emergence stage of paddy rice itself, where the paddy rice is still a young plant possessing very weak resistance against chemicals. Therefore, application of herbicides to paddy field at such stage should not be in a large amount, because each of the afore-mentioned herbicides is comparatively less selective. Under the current status, accordingly, chemicals are applied in such amount as within the range where no chemical injury is caused on rice, resulting in incomplete control of *Echinochloa crus-galli var. oryzicola*. Thus, it is said that a certain degree of *Echinochloa crus-galli var. oryzicola* is retained. In addition, emergence of *Echinochloa crus-galli var. oryzicola* lasts for a long time and therefore late emerging *Echinochloa crus-galli var. oryzicola* cannot be controlled by only once application of chemicals.

From the above-mentioned reasons, so-called systematic control is generalized in a transplanted paddy field, where the treatment with chemicals is carried out twice, i.e. before or after rice-transplantation and about 20 days after the rice-transplantation. However, if *Echinochloa crus-galli var. oryzicola* which has been kept alive after the first application of chemicals is grown to 3- to 5-leaf stage at the time when the second application of the chemicals is to be made, such *Echinochloa crus-galli var. oryzicola* cannot be controlled even by the second application and this is a problem. Therefore, there is a strong desire for the development of a herbicide which has strong power for killing aged Echinochloa spp. such as *Echinochloa crus-galli var. oryzicola*.

Further, for directly seeded paddy field, it is strongly desired to develop such herbicide as having higher selectivity between paddy rice and Echinochloa spp. and being stable to young seedling of paddy rice shortly after its emergence.

With a view to satisfying these desires, we prepared a variety of compounds and repeated herbicidal tests therewith. Among those compounds, 3-(4-(2-chloro-2-butenyloxy)phenyl)-1,1-dimethyl urea (CBPDU) of the substituted phenyl urea series was previously found to be useful but, now, as a result of our eager researches with a view to developing more excellent herbicides for use in paddy field based on the above finding, we could establish the present invention. As compared with CBPDU, the compound of the invention is more increased in the power for killing *Echinochloa crus-galli* var. *oryzicola* at the 5-leaf stage and more decreased in chemical injury on paddy rice and thus are very desirable to achieve the afore-mentioned objects and accordingly highly useful.

A series of substituted phenyl urea compounds are disclosed in Japanese Pat. No. 2329/1973 with a general formula thereof. However, the compound of the invention is not concretely illustrated in the above patent publication. It is completely new. According to the above patent publication, there are shown herbicidal properties of a series of compounds similar to that of the invention against oats, wheat, beet, chrysanthemum, beans, hemp, maize, leaf mustard, clover and foxtail with their test Examples. Such description is, however, nothing else but suggesting that the substituted phenyl urea series compounds can be used as herbicides for use in upland field. Therefore, from the description of the above Publication, no one can expect that the compound of the invention which is new and not disclosed in said patent publication has the inter-genera selectivity between paddy rice and Echinochloa spp. and further are specially effective for killing also Echinochloa spp. at the 4- to 5-leaf stage, which have been considered to be impossible for being killed with prior art herbicides. Moreover, as such substituted phenyl urea herbicides as disclosed in the above patent publication, there have been known already 3-(3,4-dichlorophenyl)-1,1-dimethyl urea (DCMU), 3-(3,4-dichlorophenyl)-1-methoxy-1-methyl urea (Linuron), etc. and these herbicides are used as those for use in upland field. In order to inhibit the Hill reaction, these herbicides exhibit strong herbicidal activity against various weeds, giving, to the contrary, strong chemical injury to paddy rice. Thus, the known herbicides are poor in the selectivity. Although a part of the substituted phenyl urea compounds such as DCMU is used as the herbicide for use in upland field in the cultivation of a limited kind of crops, no such compound has been used actually as a herbicide for paddy rice.

The particular substituted phenyl urea of the present invention is a new compounds which, different from the known substituted phenyl urea herbicides, has high inter-genera selectivity between paddy rice and Echinochloa spp. and provides a new type of herbicide for use in paddy field. The characteristic features of the compound of the invention will be apparent from Test Examples as given herein. As shown in Test Example 1, a trans- and cis-forms and a mixture thereof in any proportion are equivalent in their activity for killing Echinochloa spp. and the selectivity to paddy rice.

The compound of the invention is superior to 3-(4-(3-chloro-2-butenyloxy)phenyl)-1,1-dimethyl urea in the herbicidal activity against *Echinochloa crus-galli var. oryzicola* at 5-leaf stage and in the viewpoint of chemical injury. Further, the former showed selectivity over a wide range. Furthermore, the compounds of this invention exhibited for superior herbicidal activity against *Echinochloa crus-galli var. oryzicola* to that of a compound disclosed in Japanese Pat. No. 2329/1973. In addition, in comparison with the known substituted phenyl urea compounds such as DCMU and Linuron which kill not only *Echinochloa crus-galli var. oryzicola* but also paddy rice and thus have non-selective activity, the compounds of this invention are quite different chemicals therefrom.

Further, as shown in Test Example 2, the compound of the invention exhibits similarly high herbicidal activity against *Echinochloa crus-galli var. oryzicola* at 1-leaf stage as the known herbicides, but the compound of the invention is able to completely kill also *Echinochloa crus-galli var. oryzicola* at 5-leaf stage, which is difficult to be killed by the known herbicides. Further, it is to be noted that in any of these cases, no chemical injury on paddy rice is caused by the compound of the invention. In the farm test carried out in a transplanted paddy field, it was found that *Echinochloa crus-galli var. oryzicola* which could not be completely killed even by a conventional systematic treatment were able to be completely killed by the application of the compound of the invention. Furthermore, also in the submerged direct seeding cultivation which is said to be a labor-saving method rice than the transplantation cultivation, the compound of the invention is able to selectively kill *Echinochloa crus-galli var. oryzicola*. Thus, it is considered that the compound of the invention contributes to the progress of the art of the agricultural field.

Acute oral toxicity $LD_{50}$ value of the compound of the invention measured on SD-strain rat is more than 2,000 mg/Kg for any of the trans-form, cis-form and a mixture thereof in equal amount and further acute fish toxicity TLm value (as defined by Official Standard issued from Ministry of Agriculture & Forestry) measured on young carp is more than 20 ppm for any of the above compounds. This proves that the compound of the invention is photosynthesis-inhibition type herbicides, exhibiting strong toxicity against Echinochloa spp. such as *Echinochloa crus-galli var. oryzicola* but being quite non-harmful to useful plants and animals such as man and cattle as well as fish, and therefore can be used quite safely as a herbicide for use in paddy field.

As explained above, the compound of the invention is by no means conceivable from the prior art and thus the present invention is established on the basis of the quite new discovery.

The compound of the invention can be prepared according to a process shown by the following reaction scheme (A):

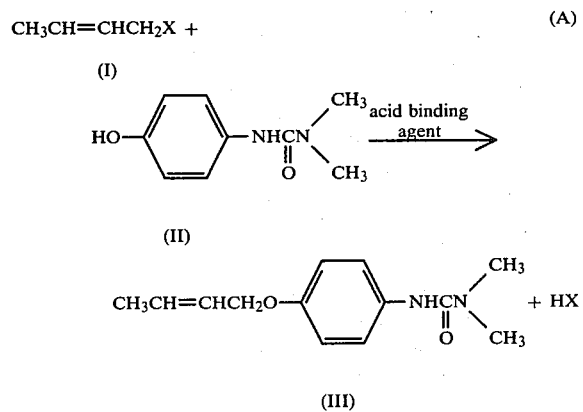

(wherein X represents a halogen atom).

A compound of the general formula (I) can easily be prepared by means of an ordinary method which comprises, for example, reacting a crotyl alcohol with a phosphorus halide or thionyl halide in the presence of a base such as pyridine, or reacting 1-butene-3-ol with a phosphorus halide or thionyl halide, accompanying allyl rearrangement. A compound of the general formula (II) can be prepared, for example, according to a process which comprises reacting a p-aminophenol with dimethylcarbamoyl chloride in the presence of an acid binding agent (cf. South Africa Pat. No. 6,803,283), a process which comprises reacting p-aminophenol with phosgene and dimethylamine (cf. British Pat. No. 1,153,261) or a process which comprises reacting p-aminophenol with diphosgene (trichloromethyl chloroformate) and dimethylamine as illustrated in Referential Preparation Example as given herein.

In the process shown by the above reaction scheme (A), the compound (I) may be used as a solvent for reacting the compound (I) with the compound (II). Ordinarily, however, an organic solvent is preferably used. As the organic solvent, almost all organic solvents such as hydrocarbons, halogen-substituted hydrocarbons, ethers, alcohols, acid amides and dimethylsulfoxides can be used. As the acid binding agent, organic amines such as triethylamine and pyridine or inorganic bases such as potassium carbonate can be used. Depending upon the kind of halogens contained in a compound (I), a catalytic amount of a salt such as potassium iodide can be added to shorten the reaction time.

The reaction may proceed even at room temperature, but generally is carried out by warming. Any temperature between room temperature and the boiling point of a solvent used can be selected and preferably the reaction is carried out at a temperature below the boiling point of a compound (I) used. The reaction time varies depending upon a compound (I) used, solvent and reaction temperature. When a polar solvent is used, the reaction will be completed in a very short period of time.

After completion of the reaction, salts of the acid binding agent are filtered off and the solvent is distilled off to give the compound of the invention (III), which alternatively is recovered by the addition of a solvent such as benzene and water.

The preparation according to the reaction scheme (A) will be illustrated in Preparation Examples 1 and 2 given herein.

Further, the compound of the invention can be prepared also according to a process shown by the following reaction scheme (B):

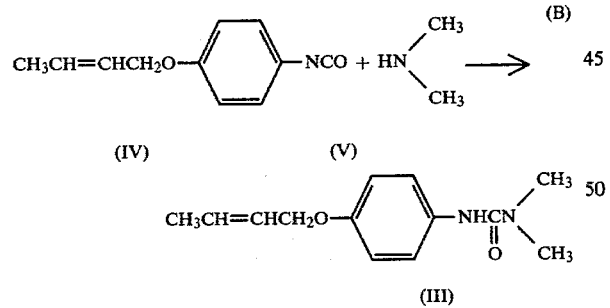

A compound of the formula (IV) can be prepared by an ordinary process which comprises reacting p-crotyloxyaniline with phosgene or diphosgene. Dimethylamine of the formula (V) may be used in either form of gas and aqueous solution.

In carrying out the process according to the above reaction scheme (B), an organic solvent such as hydrocarbons, halogen-substituted hydrocarbons or ethers is ordinarily used. When an aqueous solution of dimethylamine is used, the reaction can conveniently be carried out by using a solvent which is immiscible with water.

The reaction is generally completed in a short time, but the reaction time can be further shortened either by adding a basic substance such as trimethylamine or dibutyltin diacetate or optionally by warming. After completion of the time, the compound (III) of this invention is obtained, in general, by distilling off the solvent. Optionally, however, the product can be separated by adding a solvent such as benzene and water.

If the reaction should not be completed in the preparation of the compound (IV), a carbamoyl chloride a part or most of which is represented by the formula (VI)

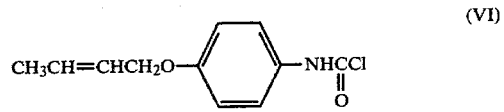

exists as a precursor. However, according to the process (B), the compound (VI) gives the compound (III) of the invention according to the process of the following reaction scheme (C) and no trouble is caused. Thus, the compound (VI) can be used in place of the compound of the formula (IV).

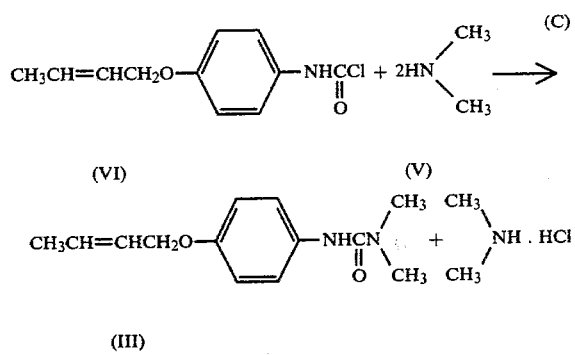

The preparation according to the above reaction scheme (C) is illustrated in Preparation Example 3 given herein.

The compounds of this invention can be prepared further according to the process shown by the following reaction scheme (D):

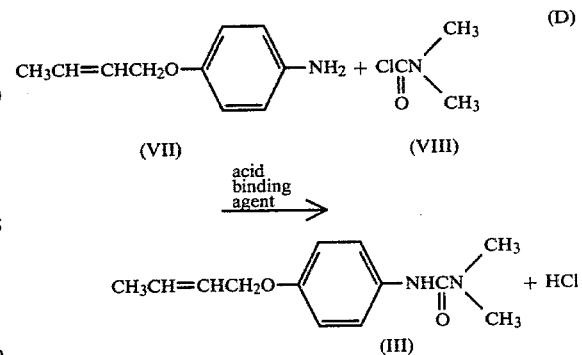

The compound of the above formula (VII) can be prepared by the reduction of p-crotyloxy-nitrobenzene which is obtained by the condensation reaction between a crotyl halide and p-nitrophenol. The compound of the formula (VIII) is prepared by an ordinary process which comprises reacting dimethylamine with phosgene or diphosgene.

In carrying out the process of the above reaction scheme (D), there are used, in general, hydrocarbons, halogen-substituted hydrocarbons or ethers as the solvent and an organic base such as triethylamine or pyridine or an inorganic base such as potassium carbonate as the acid binding agent. The reaction proceeds even at room temperature, but the reaction time is often shortened by warming. After completion of the reaction, the salts of the acid binding agent are filtered off and the solvent is distilled off to give the compound (III) of this invention. Optionally, however, a solvent such as benzene may be added to take out the end product.

The preparation according to the process of the above reaction scheme (D) is illustrated in Preparation Example 4. It is to be noted that the preparation according to this invention should not be limited to Preparation Examples given herein.

REFERENTIAL PREPARATION EXAMPLE

Preparation of 3-(4-hydroxyphenyl)-1,1-dimethyl urea

In a 2 liter-flask were placed 100 g of diphosgene (trichloromethyl chloroformate), 1 liter of ethyl acetate and 109 g of p-aminophenol were added portionwise with stirring and cooling with ice-water. After completion of the addition, the mixture was warmed and refluxed for one hour. After cooling, 180 g of 50% aqueous dimethylamine solution were added dropwise while cooling with water and, after completion of the addition, stirring at room temperature was continued for 20 minutes. The resulting crystalline mass was filtered with suction, washed with water and thereafter dried to give 148 g of the end product as white crystal (yield: 82.1%). After recrystallization from a mixed solvent of acetone and methanol, the product showed of a melting point of 205°–6° C. The compound thus obtained was used in the following Preparation Examples 1 and 2.

PREPARATION EXAMPLE 1

Preparation of 3-(4-trans-crotyloxyphenyl)-1,1-dimethyl urea

In a 300 ml-flask were placed 18.0 g of 3-(4-hydroxyphenyl)-1,1-dimethyl urea, 13.8 g of anhydrous potassium carbonate, 9.1 g of trans-crotylchloride and 100 ml of acetone and refluxed for 5 hours with stirring. After cooling, water and benzene were added, the benzene layer was taken out, thereafter washed with water and dried over anhydrous sodium sulfate. Benzene was distilled off under reduced pressure to give 22.6 g of the end product as white crystal (yield: 96.4%). After recrystallization from a mixed solvent of cyclohexane and acetone, the product melted at 115°–116° C. Chemical shift for nuclear magnetic resonance spectrum (in deuteriochloroform) was as follows:

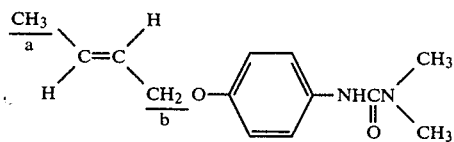

PREPARATION EXAMPLE 2

Preparation of 3-(4-cis-crotyloxyphenyl)-1,1-dimethyl urea

In a 300 ml-flask were placed 18.0 g of 3-(4-hydroxyphenyl)-1,1-dimethyl urea, 13.8 g of anhydrous potassium carbonate, 9.1 g of cis-crotyl chloride and 100 ml of acetone and refluxed for 3 hours. In a similar treatment as in Preparation Example 1, 22.8 g of the end product was obtained as white crystal (yield: 97.3%). After recrystallization from a mixed solvent of cyclohexane and acetone, the above product melted at 133°–134° C. Chemical shift for nuclear magnetic resonance spectrum (in deuterochloroform) was as follows:

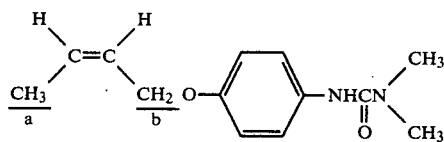

a: 1.72 ppm
b: 4.55 ppm

PREPARATION EXAMPLE 3

Preparation of 3-(4-trans-crotyloxyphenyl)-1,1-dimethyl urea 18.9 g Of 4-trans-crotyloxyphenylisocyanate were dissolved in 100 ml of benzene and 10.0 g of 50% aqueous dimethylamine solution were added dropwise while cooling with water. After completion of the addition, further stirring was effected at room temperature for 1 hour. The benzene layer was taken out, washed with water and thereafter dried over anhydrous sodium sulfate. Benzene was distilled off under reduced pressure to give 23.0 g of the end product as white crystal (yield: 98.2%). After recrystallization from a mixed solvent of cyclohexane and acetone, the above product melted at 115°–116° C.

PREPARATION EXAMPLE 4

Preparation of 3-(4-trans-crotyloxyphenyl)-1,1dimethyl urea

In a 500 ml-flask, were placed 12.9 g of dimethylcarbamoylchloride and 9.5 g of pyridine were added dropwise while cooling with ice-water. Subsequently, a solution of 16.3 g of 4-trans-crotyloxyaniline in 50 ml of chloroform was added dropwise. After completion of the addition, the above reaction mixture was warmed and refluxed for 1 hour with stirring. After cooling, the chloroform layer was taken out by adding water, washed with dilute hydrochloric acid and subsequently dilute caustic sodium and thereafter washed with water. After drying the thus treated portion over anhydrous sodium sulfate, chloroform was distilled off therefrom under reduced pressure to give 20.4 g of the end product as white crystal (yield: 87.1%). After recrystallization from a mixed solvent of cyclohexane and acetone, the product melted at 115°–116° C.

When the compound of the invention is used as a herbicide for use in paddy field, it may be used as such or by dissolving them in a suitable solvent. Preferably, similarly as ordinary herbicides, the compound of the invention is used in the form of a preparation such as granules, wettable powder or emulsion prepared with various carriers and adjuvants. Further, it is possible to enlarge the spectrum of application by mixing with any known herbicide, pesticide, bactericide or plant growth regulant.

The present invention will be further explained by the following Examples but the content of an effective component, carrier and adjuvant and the amount thereof to be added should not be limited only to those illustrated in Examples. Further, the reference to parts in the following Examples means parts by weight.

EXAMPLE 1 (GRANULES)

10 Parts of the compound of the invention (trans-form), 15 parts of bentonite, 2 parts of sodium dodecylbenzenesulfonate and 73 parts of clay were mixed thoroughly and further mixed in a kneading machine with the addition of 20 parts of water. The mixture thus obtained was granulated by passing it through a granulating machine and then dried by means of a fluidized drier to give a herbicide for use in paddy field, containing 10% of the effective component.

EXAMPLE 2

In a similar manner as Example 1, but using the cis-form in place of the trans-form, a herbicide for use in paddy field, containing 10% of the effective component was obtained.

EXAMPLE 3

In a similar manner as Example 1, but using 5 parts of the trans-form and 5 parts of the cis-form, a herbicide for use in paddy field, containing 10% of the effective component was obtained.

EXAMPLE 4 (EMULSION)

By mixing and dissolving 20 parts of the compound of this invention (trans-form), 65 parts of xylene and 15 parts of Sorbol (trade name of the emulsion manufactured by Toho Chemical Industry Co., Ltd.), a herbicidal emulsion for use in paddy field, containing 20% of the effective component was obtained.

EXAMPLE 5 (EMULSION)

In a similar manner as Example 4, but using the cis-form in place of the trans-form, a herbicidal emulsion for use in paddy field, containing 20% of the effective component was obtained.

EXAMPLE 6 (WETTABLE POWDER)

20 Parts of the compound of this invention (trans-form), 3 parts of calcium lignin sulfonate, 2 parts of polyoxyethylene nonylphenyl ether and 75 parts of clay were mixed homogeneously and ground to give a herbicidal wettable powder for use in paddy field, containing 20% of the effective component.

Further, the fact that the herbicide according to the invention for use in paddy field has high utility and thus is an excellent chemical will be proved by the following Test Examples:

Test Example 1

(Test on selectivity between Echinochloa crus-galli var. oryzicola and paddy rice)

In a Wagner pot of 1/500 are, paddy field soil (alluvial soil) was placed and 50 seeds of Echinochloa crus-galli var. oryzicola and 30 seeds of paddy rice were seeded in the surface layer of said soil and the submerging depth was kept at about 1 cm. When Echinochloa crus-galli var. oryzicola reached at the one leaf stage and 5-leaf stage, the emulsion of a predetermined concentration, prepared according to Example 4 was added dropwise. After 30 days from the treatment with the chemical, dry weights of Echinochloa crus-galli var. oryzicola and paddy rice were measured and the inhibition rate was calculated with reference to untreated area.

$$\text{Inhibition rate}(\%) = \frac{\left(\begin{array}{c}\text{Dry weight in}\\\text{untreated area}\end{array}\right) - \left(\begin{array}{c}\text{Dry weight in}\\\text{treated area}\end{array}\right)}{(\text{Dry weight in untreated area})} \times 100$$

The comparative chemicals used, i.e. DCMU and Linuron, were those commercially available, and the comparative chemicals A and B used were prepared according to the process for formulating the compound of this invention. Results obtained are shown in Table 1.

TABLE 1

| Chemicals applied | | | Dose applied (g/10 are) (amount of effective component) | Inhibition (%) by treatment at 1-leaf stage | | Inhibition (%) by treatment at 5-leaf stage | |
|---|---|---|---|---|---|---|---|
| | | | | E. crus-galli var. oryzicola | paddy rice | E. crus-galli var. oryzicola | paddy rice |
| | trans-form | | 900 | 100 | 2 | 100 | 0 |
| | | | 600 | 100 | 0 | 100 | 0 |
| | | | 300 | 100 | 0 | 100 | 0 |
| | | | 150 | 100 | 0 | 100 | 0 |
| | | | 75 | 96 | 0 | 86 | 0 |
| | cis-form | | 900 | 100 | 3 | 100 | 0 |
| | | | 600 | 100 | 0 | 100 | 0 |
| | | | 300 | 100 | 0 | 100 | 0 |
| | | | 150 | 100 | 0 | 100 | 0 |
| | | | 75 | 95 | 0 | 82 | 0 |
| Compound of this invention | | | 900 | 100 | 1 | 100 | 0 |
| | | | 600 | 100 | 0 | 100 | 0 |
| | | 4:1 | 300 | 100 | 0 | 100 | 0 |
| | | | 150 | 100 | 0 | 100 | 0 |
| | | | 75 | 94 | 0 | 80 | 0 |
| | Mixture of trans- and cis-forms | | 900 | 100 | 3 | 100 | 0 |
| | | | 600 | 100 | 0 | 100 | 0 |
| | | 1:1 | 300 | 100 | 0 | 100 | 0 |
| | | | 150 | 100 | 0 | 100 | 0 |
| | | | 75 | 96 | 0 | 83 | 0 |
| | | | 900 | 100 | 4 | 100 | 0 |
| | | | 600 | 100 | 0 | 100 | 0 |
| | | 1:4 | 300 | 100 | 0 | 100 | 0 |
| | | | 150 | 100 | 0 | 100 | 0 |
| | | | 75 | 93 | 0 | 84 | 0 |

TABLE 1-continued

| Chemicals applied | | Dose applied (g/10 are) (amount of effective component) | Inhibition (%) by treatment at 1-leaf stage | | Inhibition (%) by treatment at 5-leaf stage | |
|---|---|---|---|---|---|---|
| | | | E. crus-galli var. oryzicola | paddy rice | E. crus-galli var. oryzicola | paddy rice |
| Comparative chemicals | Comparative chemical A | 900 | 100 | 35 | 100 | 12 |
| | | 600 | 100 | 15 | 95 | 0 |
| | | 300 | 100 | 0 | 82 | 0 |
| | | 150 | 100 | 0 | 67 | 0 |
| | | 75 | 87 | 0 | 37 | 0 |
| | Comparative chemical B (compound described in Japanese Pat. Publn. No. 2329/1973) | 900 | 100 | 72 | 36 | 26 |
| | | 600 | 100 | 60 | 12 | 7 |
| | | 300 | 80 | 36 | 7 | 0 |
| | | 150 | 35 | 0 | 0 | 0 |
| | | 75 | 10 | 0 | 0 | 0 |
| | DCMU | 900 | 100 | 100 | 100 | 100 |
| | | 600 | 100 | 100 | 100 | 100 |
| | | 300 | 100 | 100 | 100 | 100 |
| | | 150 | 100 | 100 | 100 | 100 |
| | | 75 | 91 | 92 | 76 | 61 |
| | Linuron | 900 | 100 | 100 | 100 | 100 |
| | | 600 | 100 | 100 | 100 | 100 |
| | | 300 | 100 | 100 | 100 | 100 |
| | | 150 | 100 | 100 | 100 | 100 |
| | | 75 | 82 | 81 | 72 | 53 |
| Untreated area | | 0 | 0 | 0 | 0 | 0 |

In the above Test Example and the following Test Examples, the comparative chemicals A and B have the following chemical structures, respectively:

Comparative chemical A:
(CBPDU)

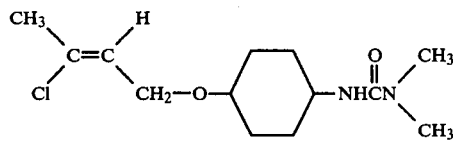

Comparative chemical B:

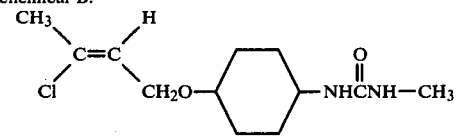

TEST EXAMPLE 2

(Test on killing effect)

In a concrete pot of 1/400 are (50 cm×50 cm), paddy field soil (alluvial soil) was placed and 200 seeds of Echinochloa crus-galli var. oryzicola were seeded in 10 surface layer of said soil and the soil was submerged at about 3 cm depth. Before emergence of Echinochloa crus-galli var. oryzicola, paddy rice at 2.5-leaf stage (Asahi species) was transplanted at the rate of 8 stubs per pot, planting 3 seedlings per stub. At the one-leaf stage (3.5 leaves stage of paddy rice) and 5 leaves stage (7 leaves stage of paddy rice) of Echinochloa crus-galli var. oryzicola, the granule prepared according to Example 1 was applied. 30 Days after the treatment with said chemical, the granule prepared according to Test Example 1 was applied. 30 Days after the treatment with the chemical, examination was made in the similar manner as Test Example 1 to obtain results as shown in Table 2.

In the table, as the comparative chemicals CPN, Benthiocarb, Molinate and Simetryne, those commercially available were used and the comparative chemicals A and B (as mentioned before) used were prepared according to the process for preparing the compound of this invention.

TABLE 2

| Chemicals applied | | Dose applied (g/10 are) (amount of effective component) | Inhibition (%) by treatment at 1-leaf stage of E. crus-galli var. oryzicola | | Inhibition (%) by treatment at 5-leaf stage of E. crus-galli var. oryzicola | |
|---|---|---|---|---|---|---|
| | | | E. crus-galli var. oryzicola | paddy rice | E. crus-galli var. oryzicola | paddy rice |
| Chemicals of this invention | trans-form | 900 | 100 | 0 | 100 | 0 |
| | | 300 | 100 | 0 | 100 | 0 |
| | | 100 | 100 | 0 | 100 | 0 |
| | cis-form | 900 | 100 | 0 | 100 | 0 |
| | | 300 | 100 | 0 | 100 | 0 |
| | | 100 | 100 | 0 | 100 | 0 |
| | trans-form + cis-form (1:1) mixture | 900 | 100 | 0 | 100 | 0 |
| | | 300 | 100 | 0 | 100 | 0 |
| | | 100 | 100 | 0 | 100 | 0 |
| | Comparative chemical - A | 900 | 100 | 23 | 98 | 5 |
| | | 300 | 100 | 0 | 72 | 0 |
| | | 100 | 100 | 0 | 48 | 0 |
| | Comparative chemical B | 900 | 100 | 40 | 30 | 7 |

TABLE 2-continued

| Chemicals applied | | Dose applied (g/10 are) (amount of effective component) | Inhibition (%) by treatment at 1-leaf stage of E. crus-galli var. oryzicola | | Inhibition (%) by treatment at 5-leaf stage of E. crus-galli var. oryzicola | |
|---|---|---|---|---|---|---|
| | | | E. crus-galli var. oryzicola | paddy rice | E. crus-galli var. oryzicola | paddy rice |
| | (compound described in Japanese Pat. Publn. No. 2329/1973) | 300 | 75 | 0 | 0 | 0 |
| | | 100 | 20 | 0 | 0 | 0 |
| Comparative chemicals | CNP | 900 | 100 | 52 | 0 | 0 |
| | | 300 | 100 | 8 | 0 | 0 |
| | | 100 | 65 | 0 | 0 | 0 |
| | Benthiocarb | 900 | 100 | 46 | 23 | 10 |
| | | 300 | 100 | 10 | 6 | 0 |
| | | 100 | 82 | 0 | 0 | 0 |
| | Molinate | 900 | 100 | 36 | 31 | 8 |
| | | 300 | 100 | 8 | 13 | 0 |
| | | 150 | 86 | 0 | 0 | 0 |
| | Simetryne | 300 | 100 | 100 | 36 | 46 |
| | | 100 | 100 | 74 | 7 | 17 |
| | | 30 | 20 | 0 | 0 | 0 |
| Untreated area | | 0 | 0 | 0 | 0 | 0 |

TEST EXAMPLE 3

(Field test in transplanted paddy field)

In a 10 m² paddy field, young seedlings of paddy rice (Asahi species) at the 2,5-leaf stage were transplanted 30 days after the puddling the submerging at the depth of 3–5 cm. 25 Days after the transplantation, when *Echinochloa crus-galli var. oryzicola* reached 4-leaf stage, a predetermined dose of the granule prepared according to Example 1 was applied. Test results were examined 60 days after the transplantation of paddy rice in the similar manner as in Test Example 1.

Comparative chemicals used were all those commercially available and in the case of the comparative chemical 2, CNP was applied 3 days after the transplantation of paddy rice and after 25 days a mixture of Benthiocarb and Simetryne was applied. Results are as shown in Table 3.

TABLE 3

| Chemicals applied | | Dose applied (g/10 are) (amount of effective component) | Inhibition (%) of E. crus-galli var. oryzicola | Inhibition (%) of paddy rice |
|---|---|---|---|---|
| Compounds of this invention | trans-form | 300 | 100 | 0 |
| | cis-form | 300 | 100 | 0 |
| | trans/cis (1:1) mixture | 300 | 100 | 0 |
| Comparative chemicals | 1. Benthiocarb + Simetryne | 210 + 45 | 25 | 0 |
| | 2. CNP → (Benthiocarb + Simetryne) | 270 → (210 + 45) | 83 | 0 |
| Untreated area | | 0 | 0 | 0 |

TEST EXAMPLE 4

(Field test in submerged directly seeded paddy field)

In a 10 m² paddy field, 30 g of *Echinochloa crus-galli var. oryzicola* seeds were seeded at the time of puddling and the depth of submerging was kept at 3–5 cm. 3 Days after the puddling, 50 g of paddy rice at the emergence stage (Asahi species) were seeded. When *Echinochloa crus-galli var. oryzicola* and paddy rice reached a 2- to 3-leaf stage, a predetermined dose of the emulsion prepared according to Example 4 was applied uniformly by means of a manual spraying machine. Test results were examined 21 days after the application of the chemicals in the similar manner as in Test Example 1.

The comparative chemical 1 used was that commercially available and the comparative chemical 2 used was prepared according to Example 4.

TABLE 4

| Chemicals applied | | Dose applied (g/10 are) (amount of effective component) | Inhibition (%) of E. crus-galli var. oryzicola | Inhibition (%) of paddy rice |
|---|---|---|---|---|
| Compounds of this invention | trans-form | 300 | 100 | 0 |
| | cis-form | 300 | 100 | 0 |
| | trans/ | 300 | 100 | 0 |

TABLE 4-continued

| Chemicals applied | | Dose applied (g/10 are) (amount of effective component) | Inhibition (%) of E. crus-galli var. oryzicola | Inhibition (%) of paddy rice |
|---|---|---|---|---|
| Comparative chemicals | cis (1:1) mixture 1. Benthiocarb | 300 | 76 | 15 |
| | 2. Molinate | 300 | 83 | 12 |
| Untreated area | | 0 | 0 | 0 |

TEST EXAMPLE 5

In a 1/7500 are Wagner pot, sieved paddy field soil (alluvial soil) was charged. Thereafter, in the center portion of the pot, 2 roots of paddy rice (Asahi species) at the 2- to 3-leaf stage were transplanted and 20 seeds of Bulrush per pot were seeded in the surface of the above soil. The pot was submerged at the depth of about 2 cm. The other *Dopatrium junceum* and umbrella plant were generated naturally. After seeding, when each of the weeds reached the same leaf age as defined in Table 5 given herein, a predetermined concentration of the emulsion prepared according to Example 4 was applied dropwise on the surface of the pot. The test was carried out by repeating the same test three times per area and the results were determined 20 days after the application of the chemicals with regard to the herbicidal effect and chemical injury on paddy rice on the basis of the evaluation index as shown below.

As the comparative chemicals Molinate, Benthiocarb and DCMU, those commercially available were used. Results obtained are as shown in Table 5.

| Evaluation index | Evaluation Standard | |
|---|---|---|
| | Degree of herbicidal effect (weed inhibition %) | Degree of chemical injury against paddy rice |
| 5 | 100 | Completely killed |
| 4 | 90–99 | Considerably injured |
| 3 | 80–89 | Moderately injured |
| 2 | 60–79 | A little injured |
| 1 | 40–59 | Slightly injured |
| 0 | less than 39 | Not injured |

In the above table, the inhibition rate was calculated according to the method as described in Test Example 1.

TABLE 5

| Compounds applied | | Dose applied (g/10a) (amount of effective component) | Weeds Leaf age | Weed kill degree | | | Chemical injury on paddy rice | Weed kill degree | | | Chemical injury on paddy rice |
|---|---|---|---|---|---|---|---|---|---|---|---|
| | | | | Bulrush | *Dopatrium junceum* | Umbrella plant | | Bulrush | *Dopatrium junceum* | Umbrella plant | |
| | | | | 3 | 2 | 2 | 3 | 3–5 | 3 | 2 | 3 tillers |
| Compounds of this invention | trans-form | 600 | | 5 | 5 | 5 | 0 | 5 | 5 | 5 | 0 |
| | | 300 | | 5 | 5 | 5 | 0 | 5 | 5 | 5 | 0 |
| | cis-form | 600 | | 5 | 5 | 5 | 0 | 5 | 5 | 5 | 0 |
| | | 300 | | 5 | 5 | 5 | 0 | 5 | 5 | 5 | 0 |
| | 1:1 mixture of trans-form & cis-form | 600 | | 5 | 5 | 5 | 0 | 5 | 5 | 5 | 0 |
| | | 300 | | 5 | 5 | 5 | 0 | 5 | 5 | 5 | 0 |
| Comparative chemicals | Molinate | 600 | | 5 | 5 | 1 | 0 | 2 | 5 | 5 | 0 |
| | | 300 | | 0 | 2 | 1 | 0 | 1 | 4 | 4 | 0 |
| | Benthiocarb | 600 | | 2 | 5 | 5 | 2 | 4 | 5 | 5 | 0 |
| | | 300 | | 0 | 5 | 2 | 2 | 3 | 5 | 5 | 0 |
| | DCMU | 600 | | 5 | 5 | 5 | 5 | 5 | 5 | 5 | 5 |
| | | 300 | | 5 | 5 | 5 | 5 | 5 | 5 | 4–5 | 4 |
| Untreated area | | 0 | | 0 | 0 | 0 | — | 0 | 0 | 0 | — |

What we claim is:

1. 3-(4-Crotyloxyphenyl)-1,1-dimethyl urea.
2. The compound as claimed in claim 1, wherein it is in the trans-form.
3. The compound as claimed in claim 1, wherein it is in the cis-form.
4. A herbicidally active composition for use in a paddy field, which comprises a herbicidally effective amount of 3-(4-crotyloxyphenyl)-1,1-dimethyl urea in a herbicidal carrier.

* * * * *